US 12,121,222 B2
Oct. 22, 2024

(54) PHYSICAL ASSESSMENT DEVICE

(71) Applicant: Welch Allyn, Inc., Skaneateles Falls, NY (US)

(72) Inventors: David M. Babson, Warners, NY (US); James Ledwith, Syracuse, NY (US); Kenneth V. Coon, Jordan, NY (US); Eric Samsel, Cicero, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 269 days.

(21) Appl. No.: 17/655,798

(22) Filed: Mar. 22, 2022

(65) Prior Publication Data

US 2022/0330803 A1 Oct. 20, 2022

Related U.S. Application Data

(60) Provisional application No. 63/201,221, filed on Apr. 19, 2021.

(51) Int. Cl.
*A61B 1/227* (2006.01)
*A61B 1/06* (2006.01)
*H05B 45/10* (2020.01)

(52) U.S. Cl.
CPC ............. *A61B 1/227* (2013.01); *A61B 1/06* (2013.01); *A61B 1/0684* (2013.01); *H05B 45/10* (2020.01)

(58) Field of Classification Search
CPC ......... A61B 1/227; A61B 1/06; A61B 1/0684; A61B 1/00034; A61B 1/00036; A61B 3/12; A61B 1/0004; A61B 1/00039; A61B 3/0008; A61B 2560/0431; H05B 45/10; H04N 23/56; H04N 23/74
See application file for complete search history.

(56) References Cited

U.S. PATENT DOCUMENTS

| | | |
|---|---|---|
| 7,871,407 B2 | 1/2011 | Howell |
| 8,786,210 B2 | 7/2014 | Delucia |
| 9,089,296 B2 | 7/2015 | Heine et al. |
| 9,526,481 B2 | 12/2016 | Storz et al. |
| 9,839,086 B2 | 12/2017 | Merkt et al. |
| 9,986,212 B2 | 5/2018 | Schneider et al. |
| 10,278,681 B2 | 5/2019 | Wood et al. |

(Continued)

FOREIGN PATENT DOCUMENTS

| | | |
|---|---|---|
| CN | 207135319 U | 3/2018 |
| DE | 20 2010 004 123 U1 | 4/2011 |

(Continued)

OTHER PUBLICATIONS

Extended European Search Report for Application No. 22168552.2 dated Sep. 22, 2022.

*Primary Examiner* — Monica C King
(74) *Attorney, Agent, or Firm* — Merchant & Gould P.C.

(57) ABSTRACT

An instrument head for attachment to a plurality of instrument handles having different power sources is described. The instrument head includes at least one light-emitting diode, and a controller. When the controller detects an instability in a voltage input from a power source in an instrument handle attached to the instrument head, the controller transitions from a normal mode of operation to a mitigation mode of operation. The mitigation mode of operation prevents an increase in output of the at least one light-emitting diode for a predetermined period of time.

19 Claims, 6 Drawing Sheets

(56) References Cited

U.S. PATENT DOCUMENTS

| | | | |
|---|---|---|---|
| 10,675,028 B2* | 6/2020 | Shelton, IV | A61B 34/76 |
| 11,867,566 B2* | 1/2024 | Lane | G01K 1/20 |
| 2004/0183482 A1 | 9/2004 | Roberts et al. | |
| 2014/0062319 A1* | 3/2014 | Huang | H05B 45/375 |
| | | | 315/186 |
| 2019/0216307 A1* | 7/2019 | Coon | A61B 1/00124 |
| 2022/0233065 A1* | 7/2022 | Babson | A61B 3/0091 |
| 2022/0330789 A1* | 10/2022 | Babson | A61B 1/00066 |
| 2022/0330793 A1* | 10/2022 | Babson | A61B 3/1208 |
| 2022/0330803 A1* | 10/2022 | Babson | A61B 1/06 |

FOREIGN PATENT DOCUMENTS

| | | | | |
|---|---|---|---|---|
| DE | 10 2015 108 217 B3 | 9/2016 | | |
| TW | 201223069 A * | 6/2012 | | B60L 3/0046 |
| WO | 2019/143668 A1 | 7/2019 | | |
| WO | 2021/048840 A1 | 3/2021 | | |

* cited by examiner

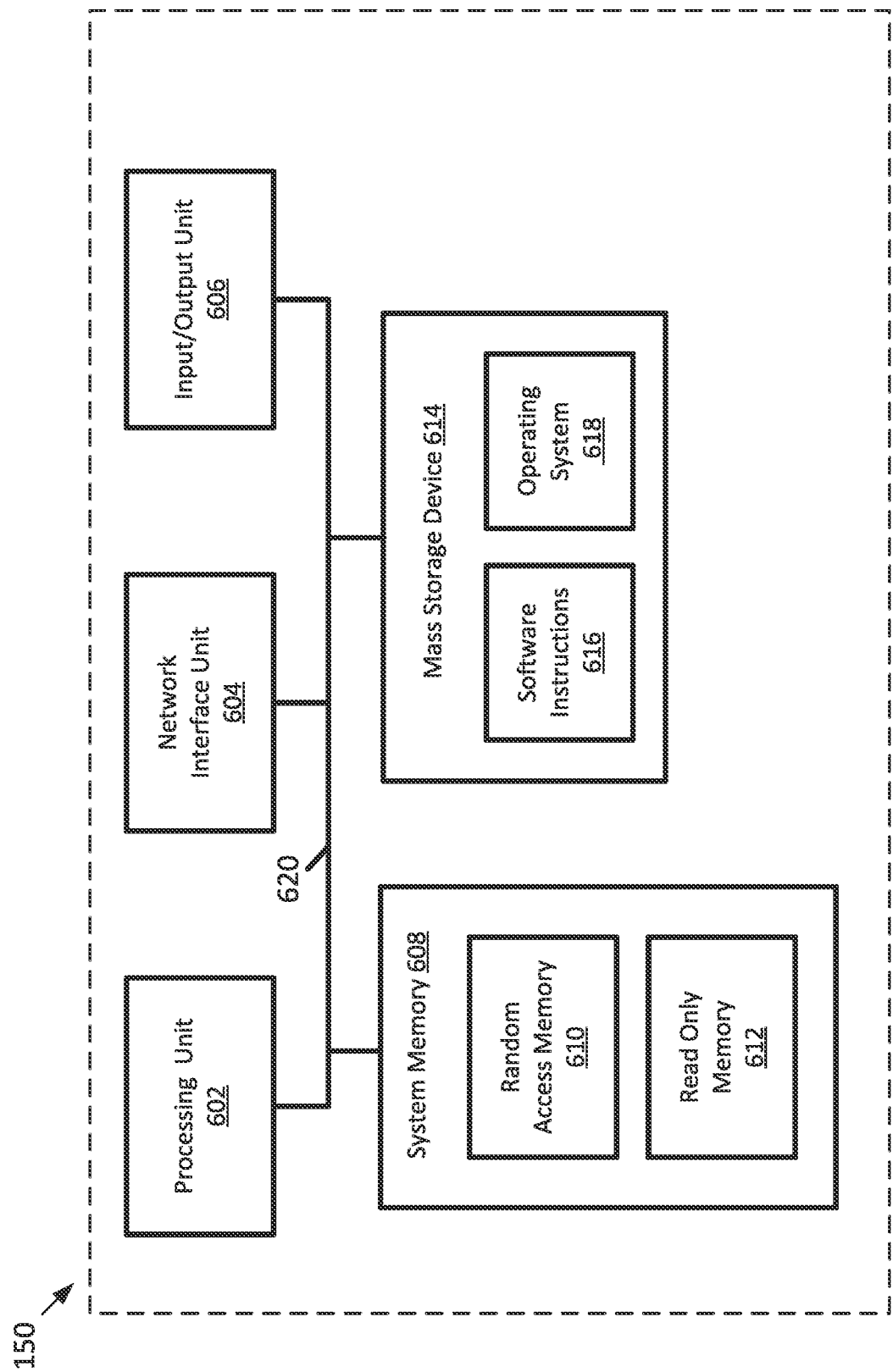

PHYSICAL ASSESSMENT DEVICE

BACKGROUND

Physical assessment devices are used for examining patients as part of wellness visits and/or routine examinations. These devices include, among others, an otoscope for diagnosing conditions of the ear, an ophthalmoscope for diagnosing conditions associated with the eye of a patient, and a dermatoscope for examining the skin of a patient.

Each of these physical assessment devices typically includes an instrument head that is releasably attached to the upper end of an instrument handle. The instrument head typically includes an illumination source and optics that enable a physician to view a medical target, such as an ear or eye, through an eyepiece. The instrument handle contains a power source that powers the illumination source and other components of the instrument head. Different instrument handles may include different power sources such as rechargeable batteries, disposable batteries, or may provide power from wall mounted transformers.

SUMMARY

In general terms, the present disclosure is directed to the field of diagnostic medicine and more specifically to an improved physical assessment device configured to perform diagnostic patient examinations. In certain examples, the physical assessment device is an otoscope, an ophthalmoscope, or other similar diagnostic device. Various aspects are described in this disclosure, which include, but are not limited to, the following aspects.

One aspect relates to an instrument head for attachment to a plurality of instrument handles having different power sources. The instrument head comprises at least one light-emitting diode; and a controller having one or more processing units and a memory storing instructions which, when executed by the one or more processing units, cause the controller to detect an instability in a voltage input from a power source in an instrument handle when attached to the instrument head, the voltage input powering the at least one light-emitting diode; and transition from a normal mode of operation to a mitigation mode of operation when the instability is detected, the mitigation mode of operation preventing an increase in output of the at least one light-emitting diode for a predetermined period of time.

Another aspect relates to a physical assessment device, comprising an instrument handle supplying a voltage input from a power source; and an instrument head attached to the instrument handle, the instrument head including: at least one light-emitting diode; and a controller having one or more processing units and a memory storing instructions which, when executed by the one or more processing units, cause the controller to: detect an instability of the voltage input from the power source; and transition from a normal mode of operation to a mitigation mode of operation in response to detecting the instability, the mitigation mode of operation preventing an increase in output of the at least one light-emitting diode.

Another aspect relates to a method of powering at least one light-emitting diode on an instrument head, the method comprising detecting an instability of a voltage input received from an instrument handle when attached to the instrument head, the voltage input powering the at least one light-emitting diode; transitioning from a first mode of operation to a second mode of operation in response to detecting the instability, the second mode of operation preventing an increase in output of the at least one light-emitting diode for a first predetermined period of time; detecting a rapid lowering of the voltage input; transitioning from the first mode of operation to a third mode of operation in response to detecting the rapid lowering, the third mode of operation allowing only a decrease in output of the at least one light-emitting diode for a second predetermined period of time; detecting that the voltage input is below a threshold amount; and transitioning from the first mode of operation to a fourth mode of operation in response to detecting that the voltage input is below the threshold amount, the fourth mode of operation disabling the at least one light-emitting diode for a third predetermined period of time.

DESCRIPTION OF THE FIGURES

The following drawing figures, which form a part of this application, are illustrative of the described technology and are not meant to limit the scope of the disclosure in any manner.

FIG. 6 schematically illustrates an example of a controller of the instrument head of the physical assessment device of FIG. 1.

DETAILED DESCRIPTION

Figure 1:
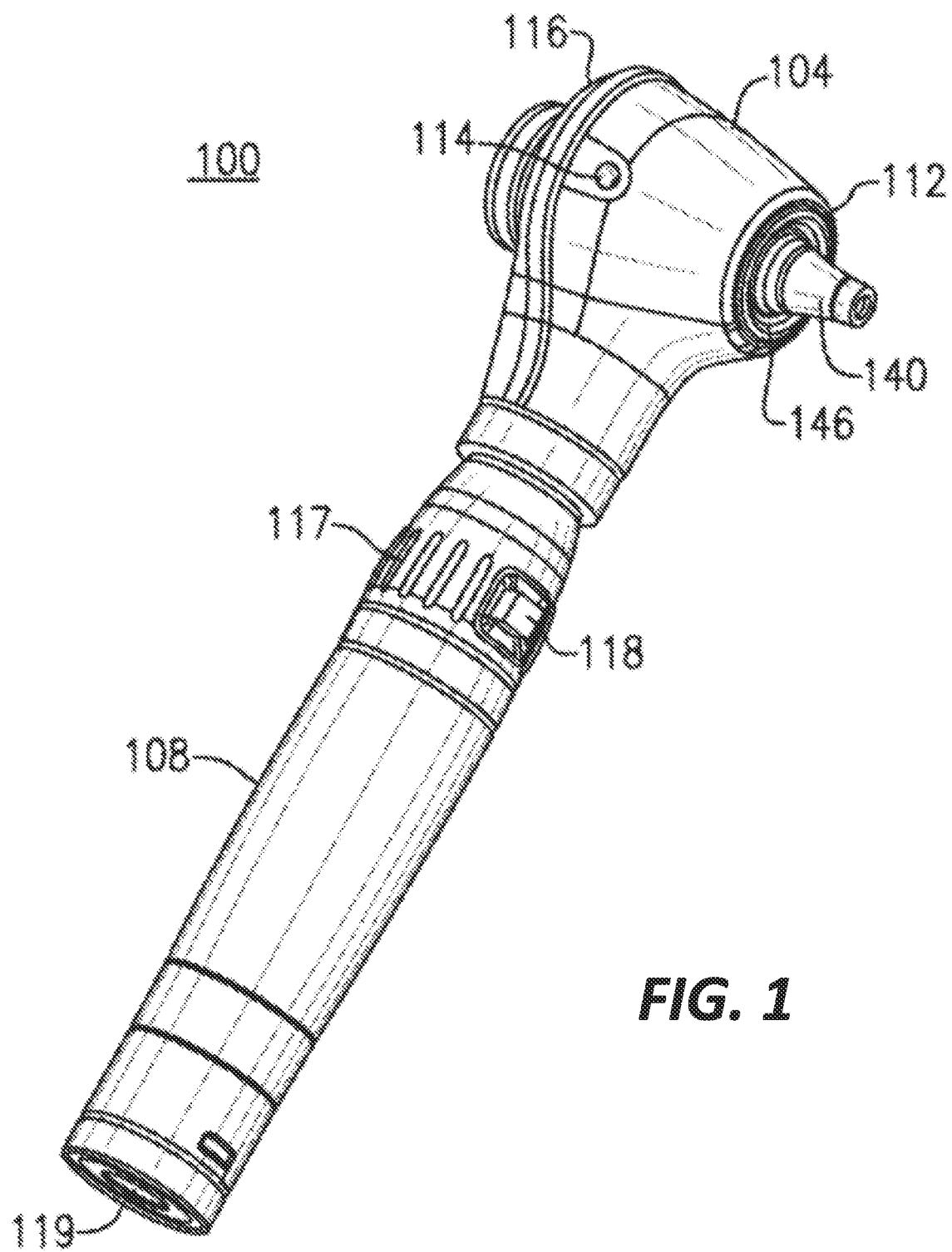
FIG. 1 is an isometric view of an example of a physical assessment device.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is an isometric view of a physical assessment device 100. The physical assessment device 100 may share similar components with the physical assessment devices described in U.S. patent application Ser. No. 16/248,482, titled Physical Assessment Device, filed on Jan. 15, 2019, the entirety of which is hereby incorporated by reference.

In the example illustrated in FIG. 1, the physical assessment device 100 is an otoscope. In other alternative examples, the physical assessment device 100 is an ophthalmoscope, a dermatoscope, or other type of physical assessment device.

The physical assessment device 100 includes an instrument head 104 that is releasably attached to the upper end of an instrument handle 108. The instrument handle 108 is sized and shaped to permit the physical assessment device 100 to be handheld and is further configured to contain a power source for powering the instrument head 104.

A light source of the instrument head 104 is energized by the instrument handle 108. The illumination output of the light source is controlled by a rheostat 117, which includes a twistable dial 118 formed on the instrument handle 108.

The twistable dial 118 can be twisted by the hand of the user to adjust the illumination output of the light source.

The power source can be recharged via a charging port 119. In the example shown in FIG. 1, the charging port 119 is provided on the bottom end of the instrument handle 108.

Figure 2:
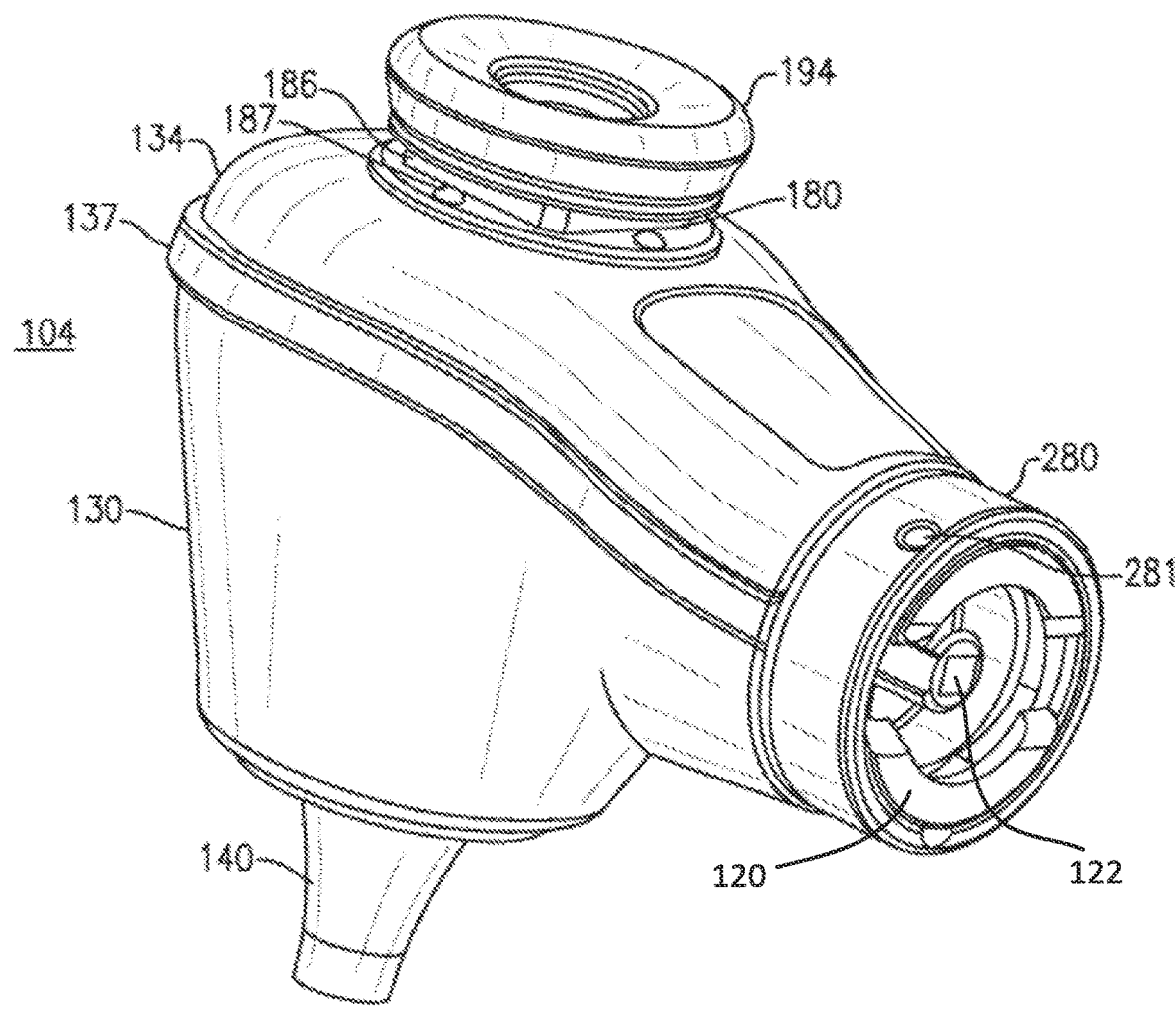
FIG. 2 is an isometric view of an example of an instrument head of the physical assessment device of FIG. 1.

FIG. 2 is a bottom isometric view of an instrument head. Referring now to FIGS. 1 and 2, the instrument head 104 includes a body housing having a distal patient end 112 and an opposing proximal caregiver end 116. The interior of the instrument head 104 is sized and configured to retain a plurality of components. The physical assessment device 100 retains an optical assembly that includes a hollow lens tube containing a plurality of optical components that are supported within the interior of the instrument head 104.

The instrument head 104 includes a pair of mated housing sections that include a front housing section 130 and a rear housing section 134. Each of the front and rear housing sections 130, 134 is a shell-like member made from a structural material, such as a moldable plastic. The front and rear housing sections 130, 134 can be mated to one another using fasteners to define an interior cavity. Alternatively, the front and rear housing sections 130, 134 can also be secured by welding, such as ultrasonic welding or other suitable means.

The lower ends of each of the front and rear housing sections 130, 134 are retained at the bottom of the instrument head 104 using a securing ring 280. According to this embodiment, a peripheral bumper 137 is disposed between the front and rear housing sections 130, 134. In some examples, the securing ring 280 can include a locking element, such as, for example, a pin that is insertable through a transverse opening 281 formed in the securing ring 280.

A hollow speculum tip element, that is designed and shaped to fit a predetermined distance into the ear canal, can releasably attach to a distal ring member 146. When attached, the hollow speculum tip element overlays a distal insertion portion 140 on the distal patient end 112. The distal insertion portion 140 includes an optical window, and an objective lens is positioned adjacent the optical window inside the body housing of the instrument head 104.

The opposing proximal caregiver end 116 includes an adapter interface member 180 that is configured to receive an adapter for attaching an external device to the instrument head 104. In the example illustrated in FIG. 2, the adapter interface member 180 includes machined flats 186 and spring loaded balls 187 that can provide a stable mounted platform for the adapter. The adapter interface member 180 can also include a brow rest 194.

A bottom portion of the instrument head 104 includes a mechanical interface 120 and an electrical interface 122. In the example shown in the figure, the mechanical interface 120 is a ring that can engage a corresponding mechanical interface on the instrument handle 108 to attach the instrument handle 108 to the instrument head 104. In the example shown in the figure, the electrical interface 122 is a pin that can engage a corresponding electrical interface on the instrument handle 108 to provide an electrical connection with the instrument handle 108.

Typically, instrument heads are compatible only with specific instrument handles. This is because instrument heads typically have distinct types of lighting assemblies that have different electrical requirements. For example, some types of instrument heads have light assemblies that are halogen lamp based. A halogen lamp filament becomes brighter when an input voltage increase, and the lamp filament dims when the input voltage decreases.

In contrast, other types of instrument heads have light assemblies that are light-emitting diode (LED) based. Varying voltage as a way of controlling illumination output is incompatible with LEDs. Instead, LED light dimming is achieved by a constant current that is pulse-width modulated to reduce the duty time that the LED is on.

In addition, traditional instrument handles may include alternating current (AC) power sources, and may only be compatible with lighting that can use AC power, such as incandescent or halogen lighting. Further, different instrument handles may be wired with different polarities, requiring the instrument heads to be hardwired to accept the specific polarity. LED drive circuits have strict requirements for polarity. Current instrument handles have multiple polarities (+/−, −/+ and a variation of AC), and therefore the input power must be rectified to a single polarity before an LED in the instrument head can be driven.

Thus, instrument handles are typically designed to provide electrical power in a specific voltage profile and current based on the requirements of the light assemblies provided on the instrument heads. Accordingly, instrument heads are not typically usable with different instrument handles, requiring a proliferation of instrument heads and handles.

The following description relates to software control and algorithms that allow compatibility between different instrument heads and instrument handles. More specifically, the software control and algorithms are implemented on the instrument head 104 to adapt the instrument head 104 to be compatible with distinct types of instrument handles. The software control allows the instrument head 104 to be compatible with instrument handles designed for powering halogen lamps and with instrument handles designed for powering LEDs.

Figure 3:
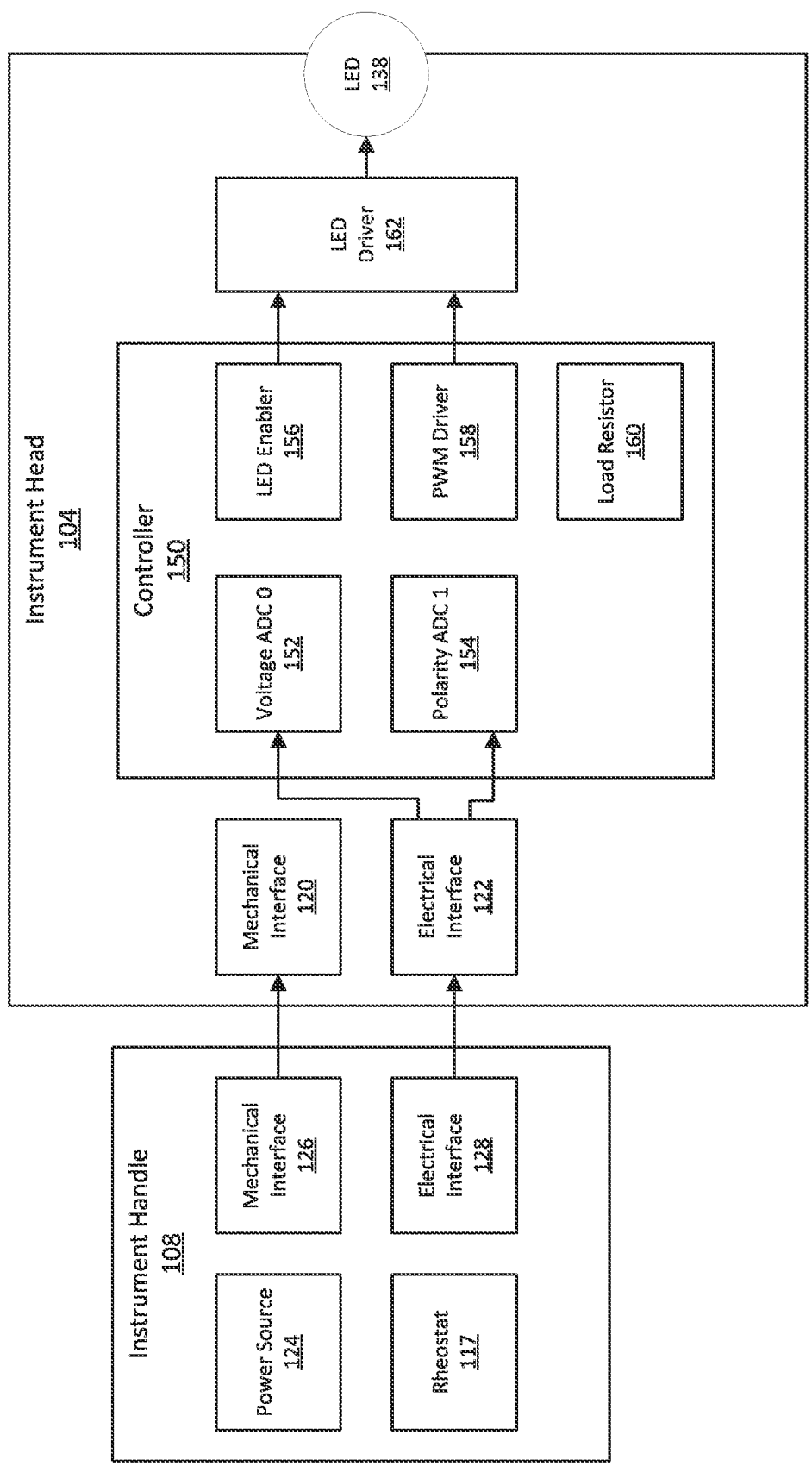
FIG. 3 schematically illustrates the physical assessment device of FIG. 1.

FIG. 3 schematically illustrates the physical assessment device 100. As discussed above, the physical assessment device 100 includes the instrument handle 108 and the instrument head 104. The instrument handle 108 includes the rheostat 117, and a power source 124. The power source 124 can include one or more rechargeable batteries or disposable batteries, or can be acquired from a 120-volt power outlet or from a Universal Serial Bus (USB) connector. The rheostat 117 can be operated by a user to control the current from the power source 124.

The instrument handle 108 includes a mechanical interface 126 that can releasably attach to the mechanical interface 120 of the instrument head 104 to fix the instrument handle 108 to the instrument head 104. Thus, a user can grasp the instrument handle 108 with the instrument head 104 attached thereto to perform an otoscopic or ophthalmic examination. In some examples, the mechanical interface 126 also provides grounding.

The instrument handle 108 further includes an electrical interface 128 that interfaces with the electrical interface 122 of the instrument head 104 to supply a voltage from the power source 124 to the instrument head 104. As will be described in more detail, the voltage from the instrument handle 108 is supplied to the instrument head 104 to power one or more components of the instrument head 104 including a light assembly having at least one LED 138.

As shown in FIG. 3, the instrument head 104 includes a controller 150 which includes a first analog-to-digital converter 152 and a second analog-to-digital converter 154 that both receive the voltage supplied from the power source 124 via the connection between the electrical interface 128 and electrical interface 122. The first and second analog-to-digital converters 152, 154 convert the voltage into separate, independent signals that are readable by the controller 150.

The controller 150 can use the separate, independent signals from the first and second analog-to-digital converters 152, 154 to detect voltage input instabilities from the power source 124. For example, one signal is dampened to change slowly over time while the other signal is not. The controller 150 can compare the two signals to determine whether there is an instability in the voltage input received by the instrument head 104 from the instrument handle 108.

The controller 150 includes an LED enabler 156 and a pulse-width-modulation (PWM) driver 158 that allow the controller 150 to control the illumination output of the at least one LED 138. The controller 150 also includes a load resistor 160. As will be described in more detail, the load resistor 160 can be used by the controller 150 to increase the current drawn from the power source 124 in the instrument handle 108 to help stabilize the power source 124 in the instrument handle when a voltage input instability is detected.

Figure 4:
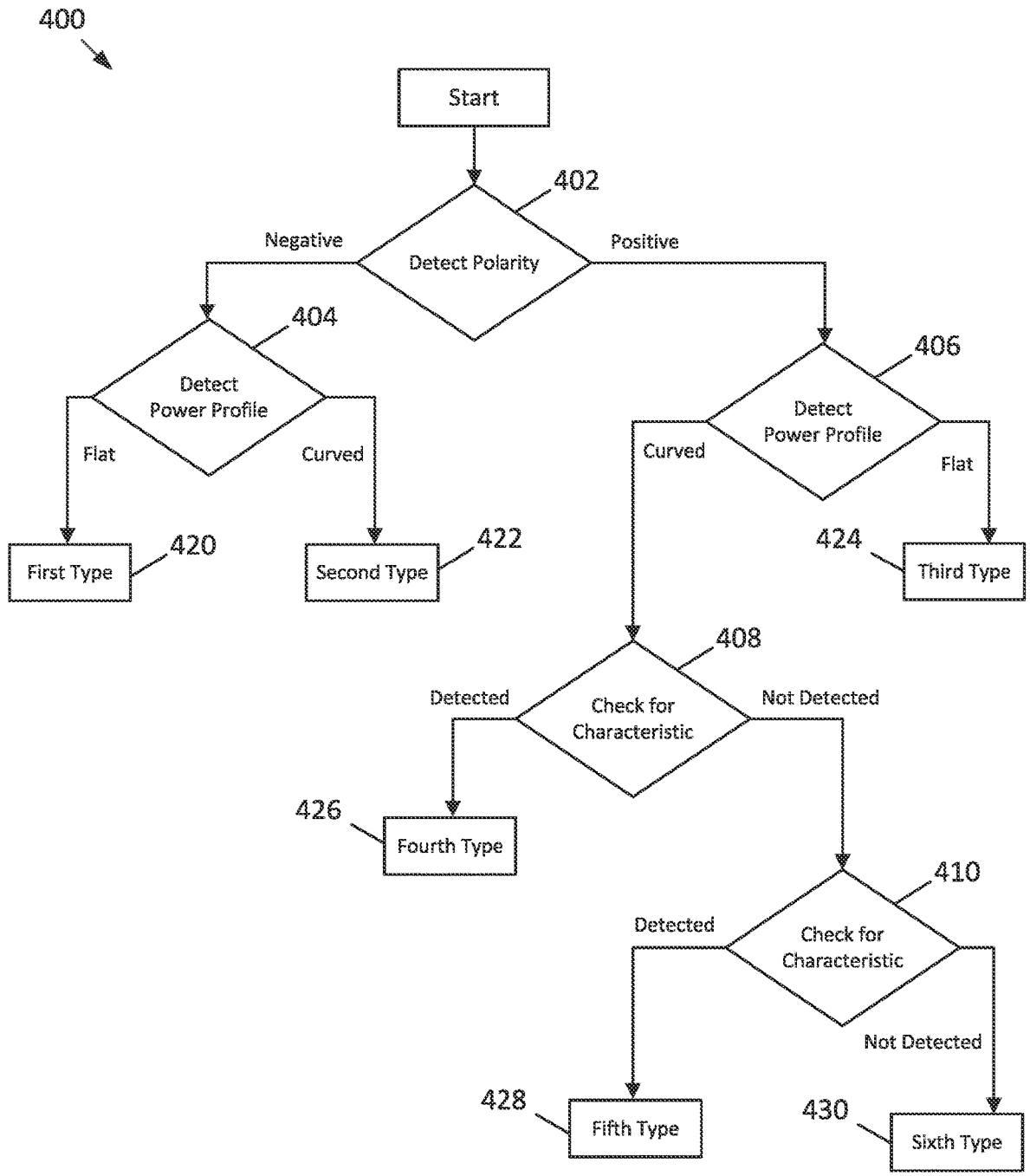
FIG. 4 illustrates a software flow diagram for identifying an instrument handle attached to the instrument head of the physical assessment device of FIG. 1.

FIG. 4 illustrates a method 400 for identifying the instrument handle 108 when attached to the instrument head 104 of the physical assessment device 100. Referring now to FIG. 4, the method 400 includes an operation 402 that determines whether the polarity of the voltage from the power source 124 in the instrument handle is negative or positive.

When the polarity is determined in operation 402 to be negative, the method 400 proceeds to an operation 404 of determining whether the power profile of the power source 124 is linear or curved (i.e., exponential). When the power profile is determined to be linear, a first type of instrument handle 420 is identified (i.e., an instrument handle having a power source with a negative polarity and a linear power profile). When the power profile is determined to be curved, a second type of instrument handle 422 is identified (i.e., an instrument handle having a power source with a negative polarity and a curved power profile).

When the polarity is determined in operation 402 to be positive, the method 400 proceeds to an operation 406 of determining whether the power profile of the power source 124 is linear or curved (i.e., exponential). When the power profile is determined to be linear, a third type of instrument handle 424 is identified (i.e., an instrument handle having a power source with a positive polarity and a linear power profile).

When the power profile is determined in operation 406 to be curved, the method 400 proceeds to an operation 408 of determining whether a first characteristic is present in the power profile of the power source 124. In some examples, the first characteristic is a specific voltage signature. As an illustrative example, the voltage signature relates to how the voltage rises to a predetermined level of voltage. When the first characteristic is determined in operation 408 to be present, a fourth type of instrument handle 426 is identified (i.e., an instrument handle having a power source with a positive polarity, a curved power profile, and the first characteristic).

When the first characteristic is not determined in operation 408 to be present in the power profile, the method 400 proceeds to an operation 410 of determining whether a second characteristic is present in the power profile of the power source 124. In some examples, the second characteristic is a pulsed signal that is pulse-width-modulated.

When the second characteristic is determined in operation 410 to be present, a fifth type of instrument handle 428 is identified (i.e., an instrument handle having a power source with a positive polarity, a curved power profile, and the first characteristic). When the second characteristic is not determined in operation 410 to be present, a sixth type of instrument handle 430 is identified (i.e., an instrument handle having a power source with a positive polarity, a curved power profile, and that does not have the first or second characteristics).

Figure 5:
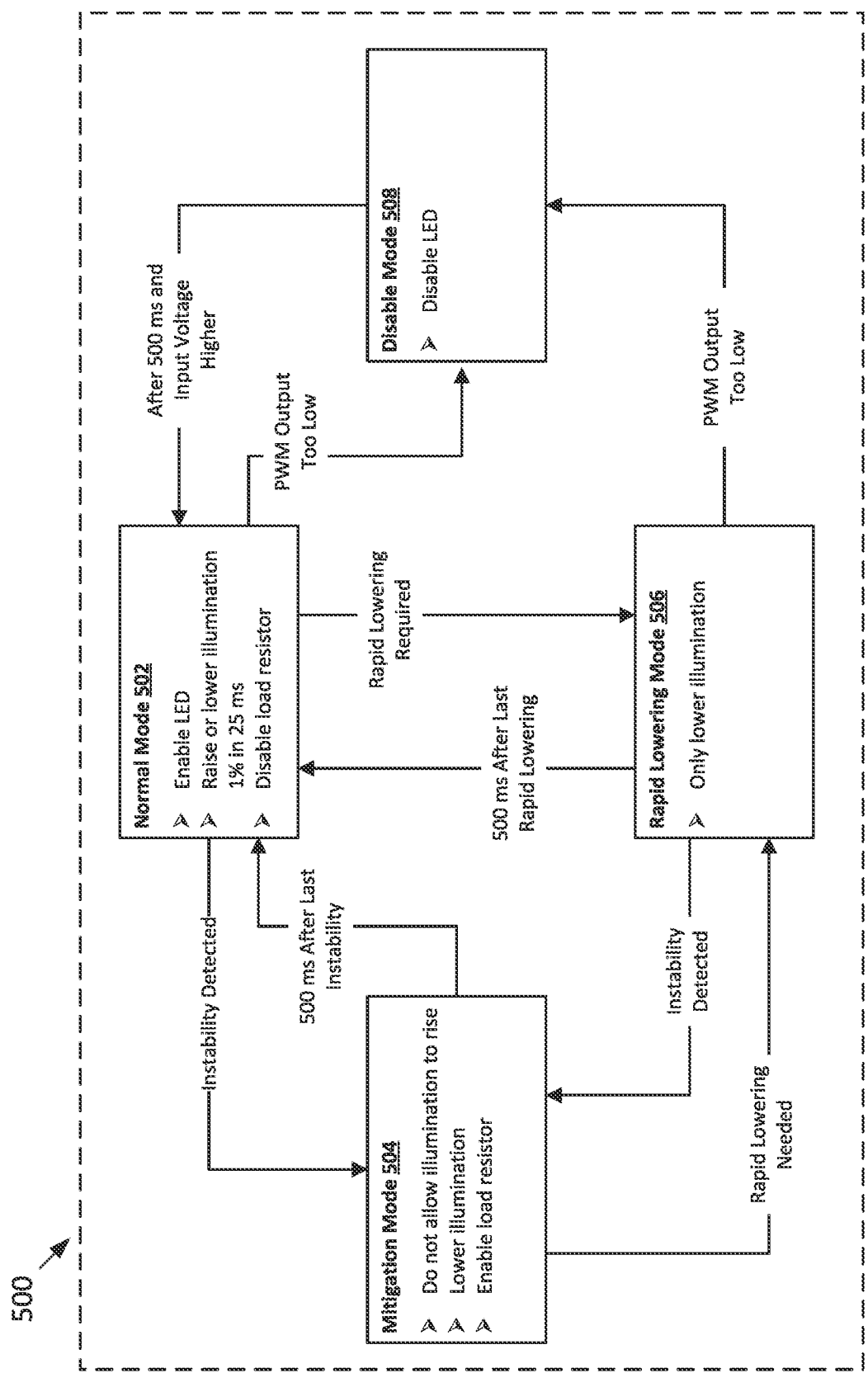
FIG. 5 schematically illustrates an algorithm for operating the instrument head of the physical assessment device of FIG. 1.

FIG. 5 schematically illustrates an algorithm 500 for operating the instrument head 104 after the instrument handle 108 has been identified from completion of the method 400. The algorithm 500 is performed by the controller 150 of the instrument head 104 (see FIG. 3) to apply control and scaling appropriate to the identified instrument handle. The algorithm 500 can be performed to dim the at least one LED 138 (see FIG. 3) proportionally with a user input using only power and return signals maintaining legacy compatibility. In this regard, the ability to identify the instrument handle connected to the instrument head 104 (by performing the method 400) enables the controller 150 to smoothly and proportionally dim the at least one LED 138. Additionally, the algorithm 500 mitigates stability problems and implements error correction. Thus, the algorithm 500 can mitigate instability for illuminating the at least one LED 138.

Incandescent or halogen bulbs draw a large amount of current whereas the at least one LED 138 does not. Thus, legacy instrument handles that are designed to power incandescent or halogen bulbs can sometimes provide an unstable voltage when powering the at least one LED 138. For example, the voltage input from legacy instrument handles can fluctuate which can cause the illumination output from the at least one LED 138 to flicker.

Referring now to FIG. 5, a normal mode of operation 502 is performed by the controller 150 to operate the at least one LED 138. The normal mode of operation 502 allows the at least one LED 138 to operate under predefined conditions that are designed to mitigate instability. As an example, the predefined conditions can include increasing or decreasing the illumination output of the at least one LED 138 by about 1% in about 25 milliseconds. In some examples, normal mode of operation 502 disables the load resistor 160 (see FIG. 3).

When an instability of the voltage received from the instrument handle 108 is detected, the controller 150 transitions from the normal mode of operation 502 to a mitigation mode of operation 504. The mitigation mode of operation 504 prevents an increase in illumination output of the at least one LED 138 for a predetermined period of time. In some examples, the mitigation mode of operation 504 lowers the illumination output of the at least one LED 138. In the mitigation mode of operation 504, the controller 150 controls the illumination output of the at least one LED 138 by controlling the PWM driver 158.

The mitigation mode of operation 504 can also enable the load resistor 160 (see FIG. 3) to increase the current being drawn from the power source 124 in the instrument handle 108. Advantageously, this can help to stabilize the power source 124 in the instrument handle 108 by imitating the current draw of a typical incandescent or halogen bulb.

In some examples, the predetermined period of time is about 500 milliseconds. After the predetermined period of time expires or once the power source 124 is detected as stable, the controller 150 transitions from the mitigation mode of operation 504 to the normal mode of operation 502. Advantageously, by identifying instabilities and switching back and forth between the normal mode of operation 502 and the mitigation mode of operation 504, the algorithm 500 can maintain a consistent illumination output and mitigate the flickering of the at least one LED.

The controller 150 can also switch from the normal mode of operation 502 to a rapid lowering mode of operation 506 to control the operation of the at least one LED 138. The rapid lowering mode of operation 506 is performed when the input voltage from the power source 124 is detected as decreasing faster than a predetermined threshold rate. The rapid decrease in the input voltage can be due to an instability from the power source 124.

In the rapid lowering mode of operation 506, the controller 150 allows the illumination output of the at least one LED 138 to decrease, and prevents the illumination output of the at least one LED 138 from increasing. The rapid lowering mode of operation 506 can be performed for a predetermined period of time. In some examples, the predetermined period of time is about 500 milliseconds. After the predetermined period of time expires or once the input voltage from the power source 124 is no longer detected as rapidly decreasing, the controller 150 transitions from the rapid lowering mode of operation 506 back to the normal mode of operation 502 to control the operation of the at least one LED 138.

The controller 150 can also transition from the rapid lowering mode of operation 506 to the mitigation mode of operation 504 when a further instability of the voltage input from the instrument handle is detected. The controller 150 can transition from the mitigation mode of operation 504 back to the rapid lowering mode of operation 506. Alternatively, the controller 150 can transition from the mitigation mode of operation 504 to the normal mode of operation 502.

The controller 150 can also switch from the normal mode of operation 502 to a disable mode of operation 508 to control the operation of the at least one LED 138. The disable mode of operation 508 is performed when the voltage input from the power source 124 is detected as being below a predetermined threshold amount. The low voltage input can affect the stability of the constant current supplied from the PWM driver 158 to the at least one LED 138.

In the disable mode of operation 508, the controller 150 disables the at least one LED 138 for a predetermined period of time. In some examples, the predetermined period of time is about 500 milliseconds. After the predetermined period of time expires or when the voltage input from the power source 124 is above the predetermined threshold amount, the controller 150 transitions from the disable mode of operation 508 to the normal mode of operation 502.

In addition to the foregoing, the controller 150 can in some instances transition from the rapid lowering mode of operation 506 to the disable mode of operation 508 when the voltage input from the power source 124 is detected as being below the predetermined threshold amount. Thereafter, the controller 150 transitions from the disable mode of operation 508 to the normal mode of operation 502 when after a predetermine period of time (e.g., 500 milliseconds) or when the voltage input from the power source 124 is above the predetermined threshold amount.

FIG. 6 schematically illustrates an example of the controller 150 that can be used by the instrument head 104 to implement aspects and features described above. In some instances, the controller 150 is a microprocessor or microcontroller. The controller 150 includes one or more processing units 602, a system memory 608, and a system bus 620 that couples the system memory 608 to the processing unit 602.

The one or more processing units 602 are examples of processing devices such as central processing units (CPUs). The system memory 608 includes a random-access memory ("RAM") 610 and a read-only memory ("ROM") 612. A basic input/output logic having basic routines that help to transfer information between elements within the controller 150, such as during startup, is stored in the ROM 612.

The controller 150 can include a mass storage device 614 that is able to store software instructions and data. The mass storage device 614 is connected to the one or more processing units 602 through a mass storage controller connected to the system bus 620. The mass storage device 614 and its associated computer-readable data storage media provide non-volatile, non-transitory storage for the controller 150.

Although the description of computer-readable data storage media contained herein refers to a mass storage device, it should be appreciated by those skilled in the art that computer-readable data storage media can be any available non-transitory, physical device or article of manufacture from which the device can read data and/or instructions. In certain embodiments, the computer-readable storage media comprises entirely non-transitory media. The mass storage device 614 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The controller 150 can operate in a networked environment using logical connections through a network interface unit 604 connected to the system bus 620. The network interface unit 604 may connect to diverse types of communications networks and devices.

The controller 150 can also include an input/output unit 606 that allows the controller to receive and process inputs and outputs from a number of external devices.

The mass storage device 614 and the RAM 610 can store software instructions and data. The software instructions can include an operating system 618 suitable for controlling the operation of the controller 150. The mass storage device 614 and/or the RAM 610 also store software instructions 616, that when executed by the one or more processing units 602, cause the controller 150 to provide the functionality discussed herein.

The various embodiments described above are provided by way of illustration only and should not be construed to be limiting in any way. Various modifications can be made to the embodiments described above without departing from the true spirit and scope of the disclosure.

What is claimed is:

1. An instrument head for attachment to a plurality of instrument handles having different power sources, the instrument head comprising:
   at least one light-emitting diode; and
   a controller having one or more processing units and a memory storing instructions which, when executed by the one or more processing units, cause the controller to:
      detect an instability in a voltage input from a power source in an instrument handle when attached to the instrument head, the voltage input powering the at least one light-emitting diode; and
      transition from a normal mode of operation to a mitigation mode of operation when the instability is detected, the mitigation mode of operation preventing an increase in output of the at least one light-emitting diode for a predetermined period of time, wherein the mitigation mode of operation causes a load resistor to increase a current drawn from the power source in the instrument handle.

2. The instrument head of claim 1, wherein the mitigation mode of operation lowers the output of the at least one light-emitting diode.

3. The instrument head of claim 1, wherein the normal mode of operation disables the load resistor, and enables the at least one light-emitting diode to operate under predefined conditions.

4. The instrument head of claim 3, wherein the predefined conditions include increasing or decreasing the output of the at least one light-emitting diode by about 1%.

5. The instrument head of claim 1, wherein the memory stores further instructions which, when executed by the at least one processor, cause the controller to:
after the predetermined period of time expires, transition from the mitigation mode of operation to the normal mode of operation.

6. The instrument head of claim 1, wherein the predetermined period of time is about 500 milliseconds from the detection of the instability.

7. The instrument head of claim 1, wherein the memory stores further instructions which, when executed by the at least one processor, cause the controller to:
detect a rapid lowering of the voltage input from the power source; and
transition from the normal mode of operation to a rapid lowering mode of operation when the rapid lowering is detected, the rapid lowering mode of operation allowing only a decrease in output of the at least one light-emitting diode for a second predetermined period of time.

8. The instrument head of claim 7, wherein the second predetermined period of time is about 500 milliseconds from the detection of the rapid lowering.

9. The instrument head of claim 1, wherein the memory stores further instructions which, when executed by the at least one processor, cause the controller to:
detect that the voltage input is below a threshold amount; and
disable the at least one light-emitting diode for a third predetermined period of time in response to detecting that the voltage input is below the threshold amount.

10. The instrument head of claim 9, wherein the third predetermined period of time is about 500 milliseconds from the detection that the voltage input is below the threshold amount.

11. The instrument head of claim 1, wherein the memory stores further instructions which, when executed by the at least one processor, cause the controller to:
detect a polarity of the power source;
detect a power profile of the power source;
detect at least one additional characteristic of the power source;
identify the power source based on the polarity, the power profile, and the at least one additional characteristic of the power source; and
based on the identified power source, convert the voltage input received from the instrument handle to a constant current for powering the at least one light-emitting diode.

12. The instrument head of claim 11, wherein the power source is a rechargeable battery, a disposable battery, or is acquired from a power outlet or USB connector.

13. The instrument head of claim 1, wherein the instrument head is a component of a physical assessment device.

14. The instrument head of claim 13, wherein the physical assessment device is an otoscope or an ophthalmoscope.

15. The instrument head of claim 1, wherein the instrument head is compatible with instrument handles that are configured for illuminating an incandescent light source, and with instrument handles that are configured for illuminating light-emitting diodes.

16. A physical assessment device, comprising:
an instrument handle supplying a voltage input from a power source; and
an instrument head attached to the instrument handle, the instrument head including:
at least one light-emitting diode; and
a controller having one or more processing units and a memory storing instructions which, when executed by the one or more processing units, cause the controller to:
detect an instability of the voltage input from the power source; and
transition from a normal mode of operation to a mitigation mode of operation in response to detecting the instability, the mitigation mode of operation preventing an increase in output of the at least one light-emitting diode, wherein the mitigation mode of operation causes a load resistor to increase a current drawn from the power source in the instrument handle.

17. The physical assessment device of claim 16, wherein the memory stores further instructions which, when executed by the at least one processor, cause the controller to:
detect a polarity of the power source;
detect a power profile of the power source;
detect at least one additional characteristic of the power source;
identify the power source based on the polarity, the power profile, and the at least one additional characteristic of the power source; and
based on the identified power source, convert the voltage input received from the instrument handle to a constant current for powering the at least one light-emitting diode.

18. A method of powering at least one light-emitting diode on an instrument head, the method comprising:
detecting an instability of a voltage input received from an instrument handle when attached to the instrument head, the voltage input powering the at least one light-emitting diode;
transitioning from a first mode of operation to a second mode of operation in response to detecting the instability, the second mode of operation preventing an increase in output of the at least one light-emitting diode for a first predetermined period of time;
detecting a rapid lowering of the voltage input;
transitioning from the first mode of operation to a third mode of operation in response to detecting the rapid lowering, the third mode of operation allowing only a decrease in output of the at least one light-emitting diode for a second predetermined period of time;
detecting that the voltage input is below a threshold amount; and
transitioning from the first mode of operation to a fourth mode of operation in response to detecting that the voltage input is below the threshold amount, the fourth mode of operation disabling the at least one light-emitting diode for a third predetermined period of time.

19. The method of claim 18, further comprising:

detecting a polarity of a power source;

detecting a power profile of the power source;

detecting at least one additional characteristic of the power source;

identifying the power source based on the polarity, the power profile, and the at least one characteristic of the power source; and converting the voltage input received from the instrument handle to a constant current for powering the at least one light-emitting diode based on the identified power source.

* * * * *